US010001410B2

(12) United States Patent
Baudelet (10) Patent No.: US 10,001,410 B2
(45) Date of Patent: Jun. 19, 2018

(54) QUANTITATIVE ELEMENTAL PROFILING IN OPTICAL EMISSION SPECTROSCOPY (71) Applicant: University of Central Florida Research Foundation, Inc., Orlando, FL (US)

(72) Inventor: Matthieu Baudelet, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 594 days.

(21) Appl. No.: 14/622,046

(22) Filed: Feb. 13, 2015

(65) Prior Publication Data
US 2015/0153225 A1 Jun. 4, 2015

Related U.S. Application Data (63) Continuation-in-part of application No. 14/334,206, filed on Jul. 17, 2014, now abandoned.

(60) Provisional application No. 61/847,370, filed on Jul. 17, 2013.

(51) Int. Cl.
*G01J 3/28* (2006.01)
*G01N 21/71* (2006.01)
*G01N 21/31* (2006.01)

(52) U.S. Cl.
CPC .............. *G01J 3/28* (2013.01); *G01N 21/718* (2013.01); *G01J 2003/283* (2013.01); *G01N 2021/3196* (2013.01)

(58) Field of Classification Search
CPC .......... G01N 21/718; G01N 2021/213; G01N 2021/3196; G01J 3/28; G01J 3/443
See application file for complete search history.

(56) References Cited

U.S. PATENT DOCUMENTS

| 8,248,072 | B1* | 8/2012 | Colson | G01N 24/08 324/309 |
| 9,606,065 | B2* | 3/2017 | Jeong | G01N 21/718 |
| 9,678,015 | B2* | 6/2017 | Fagan | G01N 21/85 |
| 2005/0254050 | A1* | 11/2005 | Fielden | G01J 3/10 356/369 |
| 2007/0211928 | A1* | 9/2007 | Weng | G01N 30/8624 382/128 |

(Continued)

OTHER PUBLICATIONS

Hübert and Ankerhold. Elemental misinterpretation in automated analysis of LIBS spectra. Analytical and Bioanalytical Chemistry. 2011. vol. 400: 3273-3278.

(Continued)

*Primary Examiner* — Jaehwan Oh
(74) *Attorney, Agent, or Firm* — Nilay J. Choksi; Smith & Hopen, P.A.

(57) ABSTRACT

The current invention considers the spectrum as a multimodal distribution over a list of structures containing the wavelength as the main entry and the other information mentioned above in the list as additional entries. Each line is then given a probability of contributing to the spectral line. In the case of multiple spectral lines, inference between spectral lines and their respective levels of confidence will provide a complete picture of the list of probable emitters with a probability factor for each line in order to provide a quantitative assignment of the spectral lines and profiling for a given spectrum.

20 Claims, 9 Drawing Sheets

(56) References Cited

U.S. PATENT DOCUMENTS

| | | | |
|---|---|---|---|
| 2009/0006002 A1* | 1/2009 | Honisch | C12Q 1/6858 702/20 |
| 2009/0162938 A1* | 6/2009 | Laine | G01N 33/5073 436/63 |
| 2010/0179435 A1* | 7/2010 | Sharifzadeh | A61B 5/14546 600/476 |
| 2011/0171636 A1* | 7/2011 | Melikechi | G01N 21/718 435/6.1 |
| 2012/0099103 A1* | 4/2012 | Hahn | G01N 21/718 356/316 |
| 2014/0168645 A1* | 6/2014 | Jeong | G01N 21/718 356/318 |
| 2014/0336971 A1* | 11/2014 | Jeong | G01N 21/718 702/104 |
| 2015/0340216 A1* | 11/2015 | Kwiecien | G06K 9/00543 250/282 |

OTHER PUBLICATIONS

Amato et al., Progress towards an unassisted element identification from Laser Induced Breakdown Spectra with automatic ranking techniques inspired by text retrieval. Spectrochimica Acta Part B. 2010. vol. 65: 664-670.

O'Leary and Kelley. Utilization of the coherence function with Welch's method for signal analysis in low resolution laser-induced breakdown spectroscopy. Applied Spectroscopy. 2010. vol. 64 (No. 4): 370-376.

ASD Data Lines Levels, National Institute of Standards and Technology: Physical Measurement Laboratory. 1999. Date Accessed Sep. 17, 2014. http://physics.nist.gov/PhysRefData/ASD/Html/lineshelp.html.

Cousin et al., Laser Induced breakdown spectroscopy library for the Martian environment. Spectrochimica Acta Part B. 2011. vol. 66: 805.

* cited by examiner

| Peak-1 | 390.067-nm | Peak-2 | 393.366-nm | Peak-3 | 394.400-nm | Peak-4 | 396.152-nm | Peak-5 | 396.847-nm |
|---|---|---|---|---|---|---|---|---|---|
| Yb-I-d6sp | 0.211981 | Ca-II-4p2P | 0.450282 | Al-I-4s2S | 0.242171 | Al-I-4s2S | 0.605156 | Ca-II-4p2P | 0.30917 |
| Th-I-* | 0.197654 | Th-I-95 | 0.276695 | Er-I-d6s2* | 0.203503 | Th-I-* | 0.075771 | Th-I-* | 0.296618 |
| Th-II-fd7p | 0.112082 | Th-II-d27p* | 0.052551 | U-I-134 | 0.071611 | Th-II-d27p* | 0.033607 | Cr-I-(4G)4py5H | 0.050838 |
| Pt-I-121 | 0.094085 | V-I-(4P)spw4D | 0.030124 | Th-II-fd7p | 0.067647 | Er-I-107 | 0.032056 | Dy-II-6p* | 0.035493 |
| Th-II-d27p* | 0.036215 | Rh-I-5pz4G | 0.027398 | Th-II-f7sp | 0.047442 | Cr-I-(4G)4py5H | 0.024868 | Sr-I-s6d3D | 0.030536 |
| Eu-I-109 | 0.031214 | Sc-I-s(3D)4p2F | 0.026641 | Th-II-f6d2* | 0.036601 | Th-II-fd7p | 0.023428 | Lu-I-ds6p*4P | 0.021868 |
| Hf-II-6pz2H | 0.030451 | Ba-I-4f3F | 0.013216 | Th-II-f26d | 0.044826 | Dy-II-189 | 0.022697 | Zr-I-5py3G | 0.019992 |
| V-I-4s4df6G | 0.054791 | Th-II-fd7p4I | 0.010698 | Ni-I-(2D)5df3G | 0.029829 | Rh-I-5pz2G | 0.017611 | W-I-* | 0.028917 |
| Th-I-13 | 0.02386 | Nd-II-d6p | 0.008253 | Re-I-* | 0.025925 | Re-I-s6py6D | 0.014586 | Y-II-d5de1F | 0.016725 |
| Tm-II-d6s | 0.021638 | Gd-I-d26p11G | 0.005469 | Er-I-58 | 0.024196 | U-I-265 | 0.010441 | Er-I-* | 0.013983 |

*FIG. 9*

QUANTITATIVE ELEMENTAL PROFILING IN OPTICAL EMISSION SPECTROSCOPY

CROSS-REFERENCE TO RELATED APPLICATIONS

This nonprovisional application is a continuation-in-part of and claims priority to U.S. Nonprovisional application Ser. No. 14/334,206, entitled "Quantitative Elemental Profiling in Optical Emission Spectroscopy", filed Jul. 17, 2014, which is a continuation of and claims priority to provisional application No. 61/847,370, entitled "Quantitative Elemental Profiting in Optical Emission Spectroscopy", filed Jul. 17, 2013, both of which are incorporated herein by reference in their entireties.

FEDERALLY SPONSORED RESEARCH OR DEVELOPMENT

This invention was made with Government support under Grant No. 2012DNBXK027 awarded by the National Institute of Justice. The government has certain rights in the invention.

BACKGROUND OF THE INVENTION

1. Field of the Invention

This invention relates, generally, to spectral analysis. More specifically, it relates to the normalization of line assignments in spectral analysis to accurately determine confidence levels of identity of elements represented by said line assignments.

2. Brief Description of the Prior Art

Spectroscopic techniques based on emission (LIBS, ICP-OES, GD-OES, Arc, Spark, etc.), rely on the assignment of the spectral peaks in a spectrum to know the composition of the material that is analyzed. The assignment of these peaks is done by looking up the peaks in a database that usually contains information, such as (1) the position of the peak in the spectrum (wavelength, wavenumber, energy, etc.); (2) the origin of the peak (emitter, absorber, vibrational mode, etc.); (3) the strength of the absorption/emission/scattering (Einstein coefficients, cross section, oscillator strength, etc.); and (4) additional technical details on the physics of the transition.

The spectral analysis is typically performed by either a practitioner or an algorithm. However, there is no quantitative evaluation of the quality of this assignment. This evaluation of the level of confidence (LOC) can be utilized in the ongoing question of accuracy and precision of assignment of a spectral line in the spectrum. What is needed is a technology that establishes such level of confidence.

The conventional art provides only the line assignment without a factor to judge the confidence in this assignment. This lack of a measure of confidence prevents a complete trust in the case of low resolution and forces the user or operator to rely on the experience, training, and skill set of a practitioner.

An example of optical emission spectroscopy, the LIBS technique, provides spectra for the possible identification and classification of compositions, such as pollutants. The use of the spectral lines in the spectrum relies on the assignment of these lines to the emitter at the origin of the emission. This assignment is done by a practitioner or an algorithm by analyzing a database for the position of the peak, its emitter and its probability (absolute or relative) of emission. However, conventional LIBS technology relies on low resolution spectra (10 pm), non-adapted databases, dynamic plasma (broadening and shifts of spectral lines [W. Hübert, G. Ankerhold, "Elemental misinterpretation in automated analysis of LIBS spectra", *Analytical and Bioanalytical Chemistry* 400(10), 3273-3278 (2011)]), and a lack of protocol (i.e., the specimen type and apparatus used affects the resultant detection limits, and as such, accuracy and precision can change from test to test depending on these factors). There is, thus, a need for a level of confidence in LIBS line assignment—an aspect that the conventional art has not contemplated.

Regarding the low resolution and interference relied upon by LIBS technology, the spectral resolution of the LIBS instrument is typically in the order of 0.01 to 0.05 nm pixel-to-pixel, in order to detect several spectral lines and still remain compact. This means that the spectral resolution is usually 0.03 to 0.15 nm. The MIT wavelength tables [G. R. Harrison, "Massachusetts Institute of Technology Wavelength tables" (1969)] establish that for "line-classification purposes", the wavenumber of a line must be known within 0.02 cm$^{-1}$ (0.02 pm for an emission at 300 nm). Even with attempts to increase this resolution by data processing [B. O'Leary, J. A. Kelley, "Utilization of the coherence function with Welch's method for signal analysis in low resolution laser-induced breakdown spectroscopy", *Applied Spectroscopy* 64(4), 370-376 (2010)], the LIBS instruments then are not suitable for an indisputable line assignment. As a result, spectral interferences are nearly unavoidable. Furthermore, the plasma conditions can involve broadening and shift of the spectral lines.

Typical databases used in optical emission spectroscopy are the MIT [G. R. Harrison, "Massachusetts institute of Technology Wavelength tables" (1969)] and NIST [ASD Data Lines Levels, National Institute of Standards and Technology: Physical Measurement Laboratory, March 1999] spectral databases, which were established by arc spectrochemical excitation. The Kurucz database, based on an atomic and molecular code, is also used.

Additionally, there is a lack of precision in tables for spectral analysis since analysis is generally qualitative. As discussed by NIST itself [ASD Data Lines Levels, National Institute of Standards and Technology: Physical Measurement Laboratory, March 1999], relative intensities are noted by authors of each publication, and thus, there is no common scale for these relative intensities. The different authors provide and use different scales, and so the relative intensities only have a meaning within the given scale or spectrum (i.e., within the spectrum of a given element in a given stage of ionization). Further, relative intensities are dependent on the light source used for the excitation. Also, the relative intensities are primarily useful for comparing strengths of spectral lines that are not widely separated, since there generally is no correction for spectral sensitivity of the measuring instruments (spectrometers, photomultipliers, photographic emulsions). Furthermore, the majority of these values are based on the MIT wavelength tables [G. R. Harrison, "Massachusetts Institute of Technology Wavelength tables" (1969), page xii], where the author explains how highly non quantitative their procedure is and where the procedure is based on "eye estimates of the lines made by observing them on a screen". In the case where the authors did not themselves measure the lines, they "adjusted the intensity values to fit [their] scale as best as [they] could", it then becomes obvious that a quantitative measure of the level of confidence cannot rely on such relative intensity values.

In the particular case of LIBS, the plasma is dynamic. Since the temperature and density of the plasma change with time, the Stark effect, in particular Stark shift and Stark broadening, evolves in time. This further hinders confidence levels in the assessment of the emitter for spectral analysis [W. Hübert, G. Ankerhold, "Elemental misinterpretation in automated analysis of LIBS spectra", *Analytical and Bioanalytical Chemistry* 400(10), 3273-3278 (2011)].

Accordingly, what is needed is a method for accurately determining a level of confidence in line assignment in order to enhance accuracy and precision of assignment of a spectral line in the spectrum. However, in view of the art considered as a whole at the time the present invention was made, it was not obvious to those of ordinary skill in the field of this invention how the shortcomings of the prior art could be overcome.

The current methodology can also rely on additional information, for example information about other spectral lines (towards full spectrum) and quantitative information about a known composition of the sample. Whereas the conventional art provides a qualitative analysis a guess), the current invention provides a quantitative analysis (i.e., the level of confidence in the assignment).

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for accurate and precise levels of confidence in spectral line assignments is now met by a new, useful, and nonobvious invention.

In an embodiment, the current invention is a tangible, non-transitory, computer-readable medium having computer-executable instructions for performing a method of running a software program on a computing device, where the computing device operates under an operating system and the method includes issuing instructions from the software program for automatically quantitatively determining a level of confidence for identification of an emitter represented by a spectral peak. Alternatively, the current invention is a computer-implemented method of automatically quantitatively determining a level of confidence for identification of an emitter represented by a spectral peak.

In either case, a spectral database containing spectral information is received. The spectral information includes spectral peak information and emitter information associated with the spectral peak information. A spectrum is loaded, including spectral peaks associated with an emitter of an analyte. The spectrum is a multimodal probability distribution over a variable, where the variable is wavelength of emitters. Possible emitters are identified as being associated with the spectral peaks, based on the spectral information in the database. The identification is based on a comparison of the spectral peaks to the information in the database, where each possible emitter has a wavelength. Emission strength (e.g., upper level population, oscillator strength (possibly included in the database), etc.) of the wavelength of each possible emitter is determined for the peaks. The emission strength is associated with the intensity of each possible emitter of the peaks. The emission strength of each possible emitter is normalized to a probability range (e.g., by multiplying the emission strength by a value of the spectrum at a wavelength of the emitter) so that a sum of the resulting probabilities of assignments of each possible emitter equals about 100% over a spectral range. The normalization of the peaks indicates emission strength of the possible emitters, such that the emission strength of each possible emitted can be used as a probability for assignment of each possible emitter with the wavelength of each possible emitter being the variable for the multimodal probability distribution in order to determine probability of the assignment of each possible emitter in the spectrum. At this point, a level of confidence of identification of each possible emitter can be determined, based on the resulting probabilities of assignment of the possible emitters. The levels of confidence for each possible emitter may, in turn, lead to a generation of a profile of the spectrum.

If multiple spectral peaks are present in the spectrum, a level of confidence may be determined for assignment of each of the peaks. In this case, an inference calculation can be performed for inference and dependency between or among the spectral peaks.

The methodology may further include correcting fir a background of the spectrum and extracting noise from the spectrum to facilitate the spectrum being a more accurate multimodal probabilistic distribution.

In a separate embodiment, the current invention can be a computer-implemented method or a tangible, non-transitory, computer-readable medium, as discussed previously. In this embodiment, a spectral database containing spectral information is received. The spectral information includes spectral peak information and emitter information associated with the spectral peak information. A spectrum is loaded, including spectral peaks associated with an emitter of an analyte. The spectrum is a multimodal probability distribution over a variable, where the variable is wavelength of emitters. A central position for each peak is defined in order to provide a density distribution for each peak in the multimodal probability distribution. A probability distribution is extracted from each density distribution, and the extracted probability distribution is compared to the spectral database to identify possible emitters that are present in the spectral peaks. Emission strength (e.g., upper level population, oscillator strength (possibly included in the database), etc.) of the wavelength of each possible emitter is determined for the peaks. The emission strength is associated with the intensity of each possible emitter of the peaks. A level of confidence is calculated for each emitter based on the emission strength of each emitter. Once a level of confidence for assignment of each peak is determined, an inference calculation is performed for inference and dependency between or among the spectral peaks. The spectral peaks are then normalized to a probability range (e.g., by multiplying the emission strength by a value of the spectrum at a wavelength of the emitter) so that a sum of the resulting probabilities of assignments of each possible emitter equals about 100% over a spectral range. The resulting probabilities indicate a probability for assignment of each possible emitter with the wavelength of each possible emitter being the variable for the multimodal probability distribution. A level of confidence of identification of each spectral peak is automatically calculated based on the resulting probabilities of assignments of the possible emitters. The levels of confidence for each possible emitter may, in turn, lead to a generation of a profile of the spectrum.

The methodology may further include correcting for a background of the spectrum and extracting noise from the spectrum to facilitate the spectrum being a more accurate multimodal probabilistic distribution.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 9 is an example of LOC after single peak analysis without correlation measurements.

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

Figure 2:
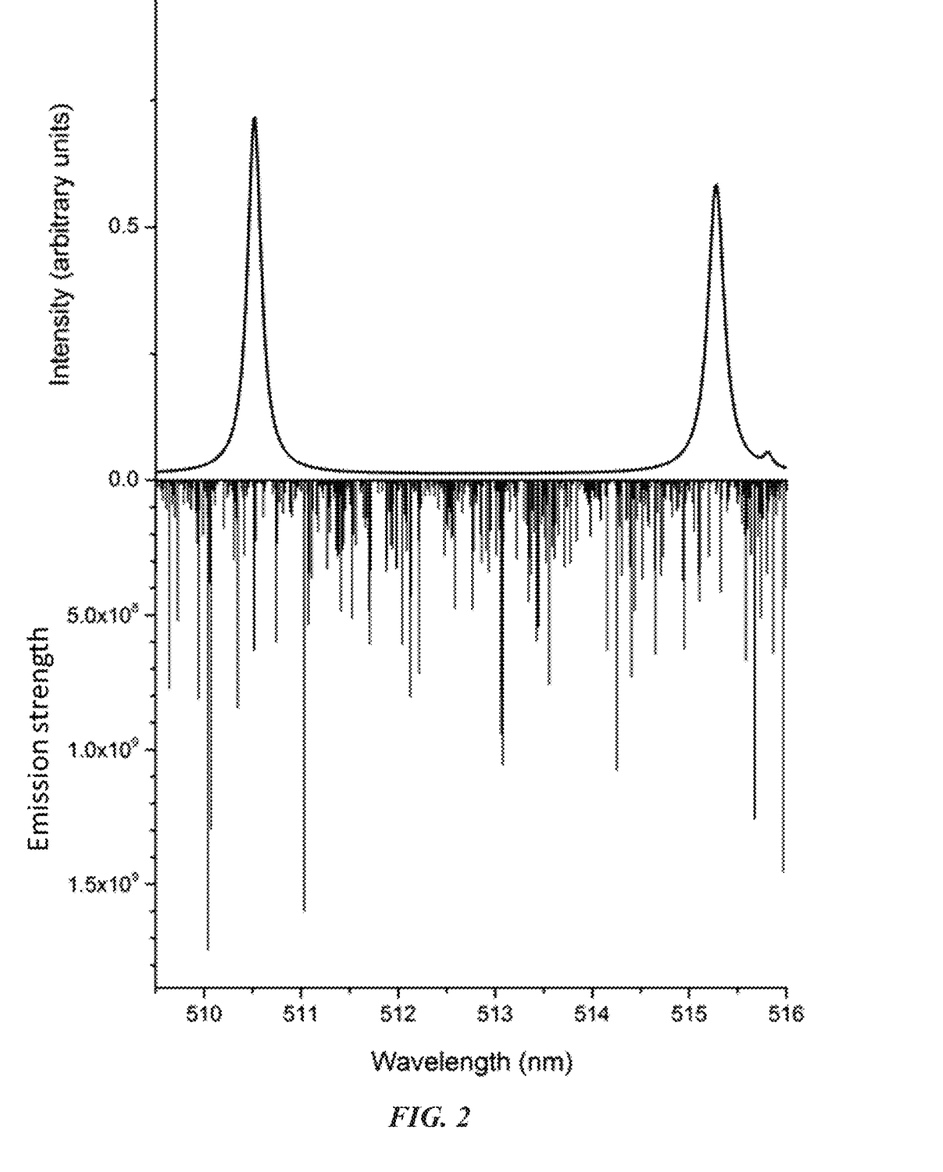
FIG. 2 depicts an example spectrum as a multimodal distribution over a list of emitters from a database.
Figure 3:
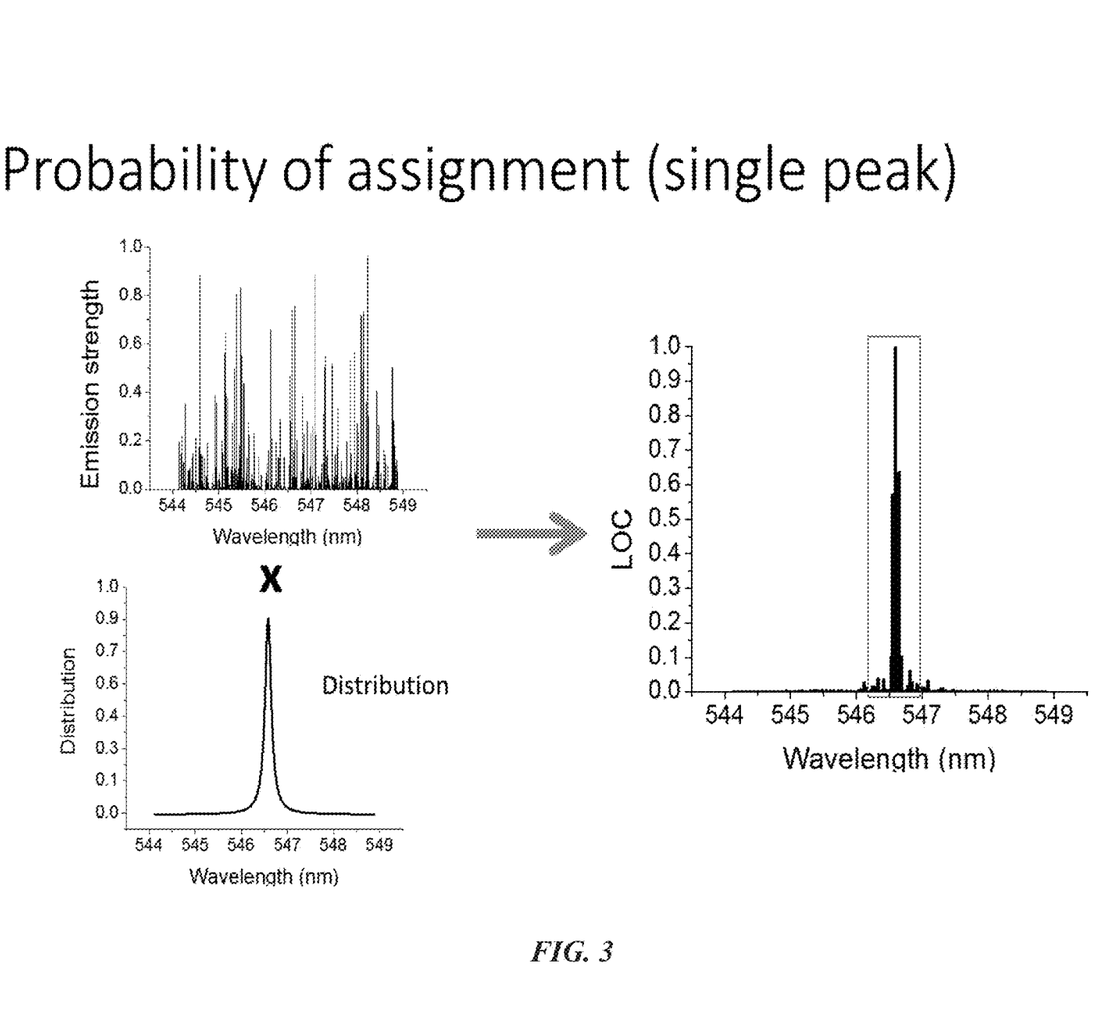
FIG. 3 is graphical illustrations depicting the probability of assignment.
Figure 4:
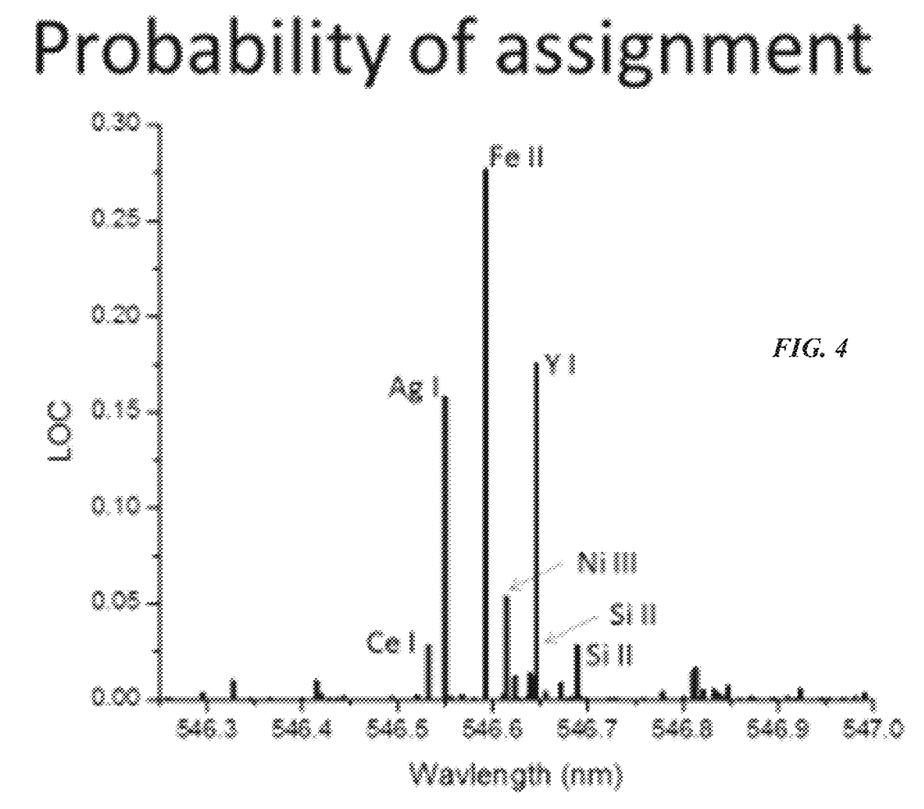
FIG. 4 is a graphical illustration depicting the probability of assignment of each element in the sample analyte.

The current invention considers the spectrum as a multimodal probability distribution over a list of structures containing the wavelength as the main entry (an example spectrum can be seen in FIG. 2). Each peak is considered as a probability distribution to derive a LOC in the assignment of an emitter for each peak. Other than wavelength, additional entries can include, but are not limited to, (1) the position of the peak in the spectrum (wavelength, wavenumber, energy, etc.); (2) the cause for the peak (emitter, absorber, etc.); (3) the strength of the process (absorption, emission, etc.) (Einstein coefficients, cross section, oscillator strength, etc.); and (4) additional technical details on the physics of the process. Each transition in the database is then given a probability of contributing to the spectral line. In the case of multiple spectral lines in the spectrum, inference between spectral lines and their respective levels of confidence would provide a further complete picture of the list of probable emitters with a probability factor for each transition in order to provide a quantitative assignment of the spectral lines and profile for a given spectrum.

The approach developed in this invention does not need to rely on input information on the resolution of the spectral analyzer but uses the spectrum as the input, in addition to eventual prior knowledge of the sample under analysis. The current invention may be implemented as a plugin in software or a stand-alone software application that provides an enhanced quantitative analysis factor for spectroscopy.

In an exemplary embodiment, the current invention can be explained with LIBS spectra. However, it is contemplated that a person of ordinary skill in the art would be able to expand and apply the invention to other spectral techniques mentioned previously. The spectrum can be seen as a multimodal probability distribution over a variable, where the primary variable is the wavelength. Each peak in the distribution can be considered as a probability distribution, which determines which wavelengths appear more probable in the spectrum. Since the distributions are not infinitely sharp, each peak defines a range of wavelengths. If the spectrum can be considered as an X-Y graph, each wavelength can be given a probability that is its Y-value of the peak (Y-value typically indicates the intensity of the signal), with the X-value being the wavelength value.

The values of the wavelengths that are important are not the ones provided by the spectrum, but the listed ones in the database. As a consequence, the spectrum becomes a multimodal distribution over a list of structures containing the wavelength as the main entry and the other information mentioned previously as additional entries.

The spectral peaks can be detected either by an algorithm according to an embodiment of the current invention or can be given by the database (or other third party) as a list of the peaks with their corresponding properties. The possible emitters can then be identified.

Figure 8:
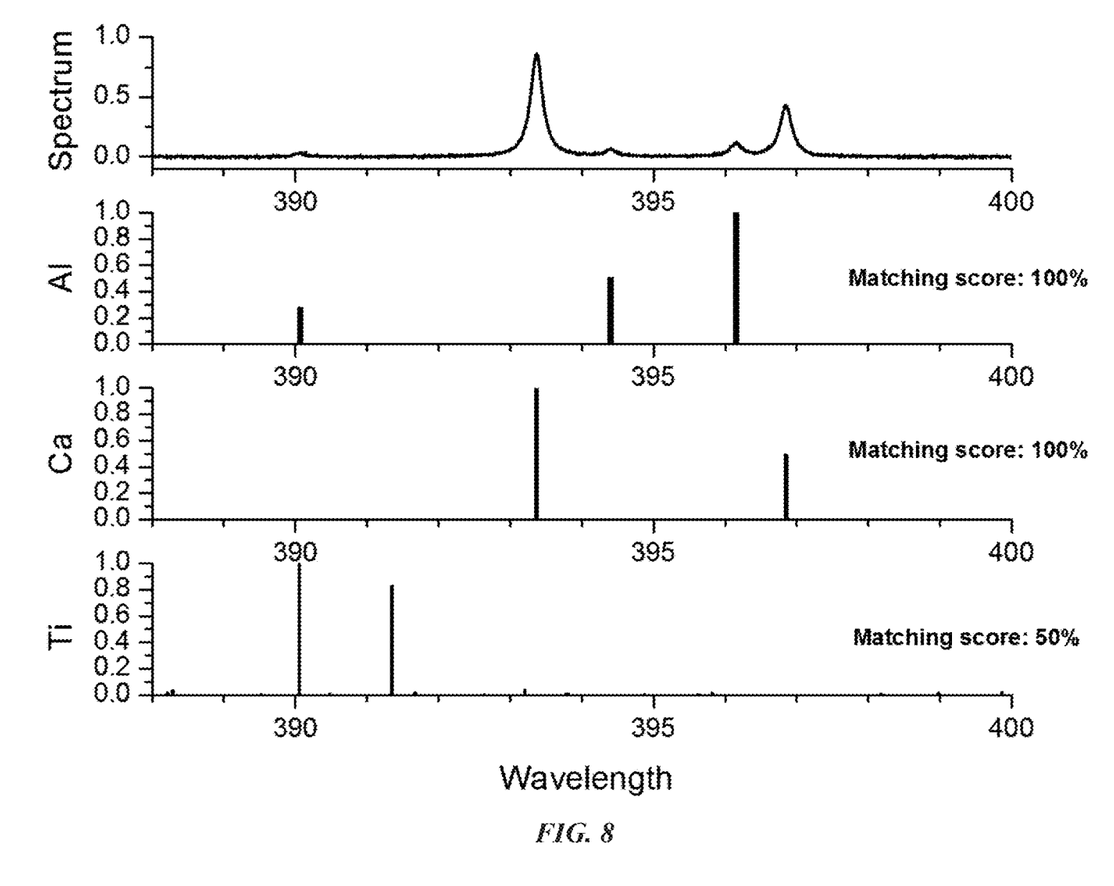
FIG. 8 depicts matching score between theoretical spectra of candidate elements and input spectrum.

The emission strength, globally represented by $N_{up}*A_{up \rightarrow low}$ for a transition as in FIG. 8, where $N_{up}$ is the population of the upper level and A is the probability of transition, can have values that depend on the degree of complexity that the practitioner needs, fir example including, but not limited, to the list as follows:

Equiprobability of transition: where each transition has the same value

Known sample composition: each element is represented by its known concentration in the sample Transition probability value: the probability of transition (e.g., given by the Einstein coefficient A, the oscillator strength f; or a relative intensity)

Figure 7:
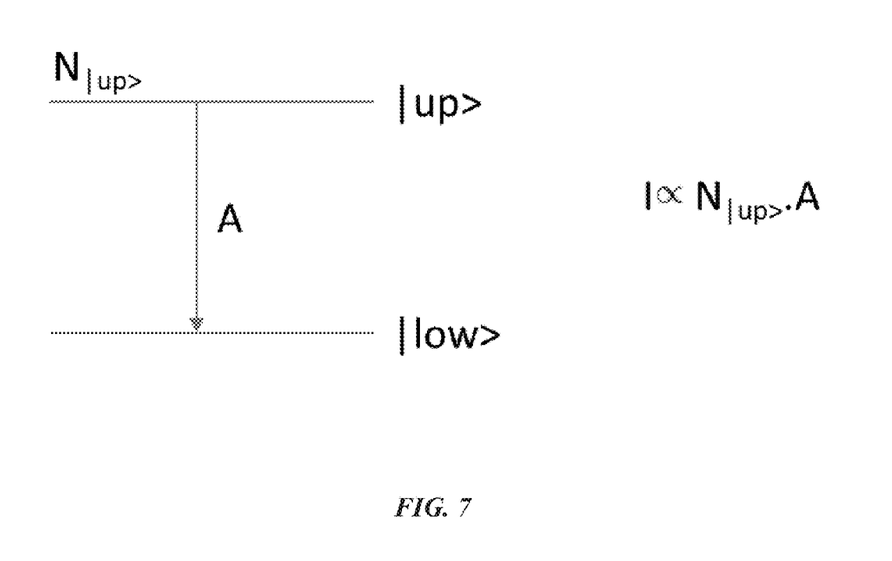
FIG. 7 depicts a transition between two levels |up> and |down>, of respective energy $E_{up}$ and $E_{down}$, and of probability A. N being the population of the upper level.

Upper level population value (see FIG. 7): where the population of the upper level is given by $N_{|up>} = N \cdot g \cdot \exp(-E_{up}/T)/Z(T)$ with N the value given to the concentration of the emitter in the plasma, g the degeneracy of the upper level, $E_{up}$ the energy of the upper level, T the temperature given/measured to/in the plasma, and Z(T) the partition function of the ion at the temperature T Modeled value of the upper level population and/or of the transition probability These different factors can be combined to provide a more precise value of the emission strength. Alternatively, the emission strength can be extracted directly from the database as the transition probability, Einstein coefficient, oscillator strength, etc. If a more complex emission strength calculation is desired, the foregoing are exemplary factors that can be utilized for facilitating calculation of the level(s) of confidence.

The calculation of a level of confidence in the assignment of each line in a spectrum relies on the knowledge of "emission strength" for each possible wavelength (transition) in the database, which also can provide energy levels for the emitters. This is mainly based on the physical process giving rise to the peak in the spectrum.

This emission strength can be given or deduced from the database. The number of emitters giving rise to the emission N can be determined at different levels of complexity from equiprobability, to knowing the population of the upper level at the origin of the emission (in plasma based techniques). The differences between the different values of N (at different complexities) influences the level of confidence and would be a condition for calculation of the level of confidence.

Once each database wavelength in the spectral range is given an emission strength weighed by the Y-value of the spectral channel as mentioned previously, normalization of each value is performed so their sum equals one (1) (or 100% for probability of assignments) over a given spectral range i.

The level of confidence can then be established for each spectral line.

In the case of a spectrum with multiple spectral lines, the first step of calculating level of confidence can be done for each line. Then inference calculation between spectral lines can be performed in order to take into account the knowledge of other lines in the calculation of the level of confidence for each line in the spectrum. Inference between two different events (here, spectral lines) is known; it is contemplated that there are many known methodologies of measuring the inference between spectral lines. Calculation of the inference determines how the LOC is modified for one spectral peak considering the other peaks in the spectrum. At this point, each spectral line of the spectrum can be given a list of probable emitters with a level of confidence for each of them.

In addition to obtaining a LOC for the assignment of each spectral peak as if they were independent, a correcting term to this "single peak LOC" can be calculated to show the inference between peaks; in other words, the single peak LOC is the value without the inference calculation and would be corrected by a term that represents the inference calculation. This correcting term takes into account the dependence of the peaks one to another in the spectrum. Such a term can be calculated before or after (or both) the "single peak LOC" calculation.

The advantages or benefits of certain embodiments of the current invention over the conventional art include, but are not limited to, increased efficiency, enhanced cost benefit, increased simplicity, and the ability to overcome a defeat. The users of such levels of confidence can then provide a quantitative evaluation of their line assignments to non-specialists who want to be aware of eventual spectral interferences for decision-making. It will enable the step of line assignments in the quantitative decision making process.

Possible uses of certain embodiments of the current invention include, but are not limited to, quantitative spectral analysis for forensic purposes, quality assurance or quality control, processes needing line assignment (e.g., plasma temperature measurements), and effective line assignments even with low resolution spectral analyzers. More specifically, an LOC provides a quantification of confidence in assignment of a spectral line when doing analysis. For example, if one wishes to show the presence of an element. The conventional art states that the practitioner's expertise must be relied upon. With the current invention, one can have a confidence level (e.g., 95%) of assigning the element to the spectral line. This can be very important, for instance, in forensic science, when one is testing for a particular element and wanted to ensure that the intensity is not interfered with from another element.

It is an object of the current invention to provide users a level of confidence for a line assignment, which, in turn, can provide a quantitative evaluation of the line assignment to non-specialists who want to be aware of eventual spectral interferences for decision making. The invention enables the step of line assignment in the quantitative decision making process.

Example

Upon receiving a spectrum (multimodal distribution over a list of emitters from a database), such as that seen in FIG. 2, individual distributions can be extracted by fitting spectral profiles (from the database) for each line (in the spectrum). The fitted spectral lines are background free, are noise free (in order to use the spectral lines later in determining level of confidence), have minimal to no overlaps (i.e., no effective amount of overlaps), and each have a line assignment. There is no assumption regarding the resolution of the spectrometers.

Figure 1:
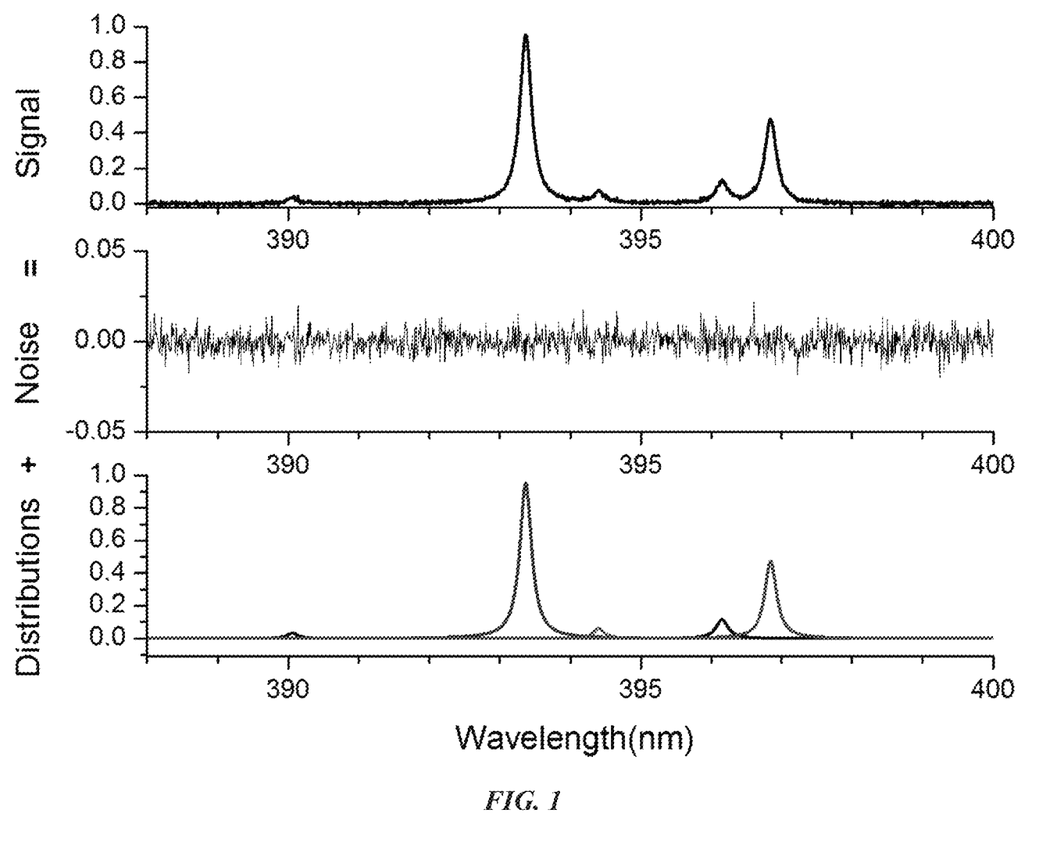
FIG. 1 is graphical illustrations depicting typical atomic emission spectrum showing the decomposition of the signal into noise and distributions components. An additional baseline component can be encountered.

The process of extracting the distribution can be seen FIG. 1. In particular, the unprocessed spectrum includes a background that is corrected for, along with noise that is extracted, and also a probabilistic distribution. Thus, once the background is corrected and noise is extracted, the probabilistic distribution remains.

Each peak is attributed with a list of emitters, each of them having an emission strength, interpreting the probability of each emitter to be at the origin of that spectral line.

The correlation between spectral lines can be defined by different algorithms/models/databases. A set of spectral lines is given for each element/set of elements, and a measurement of the correlation between the number of expected transitions and measured transitions provides a ranking of the more probable elements to be at the origin of the spectrum. This can be done such as in FIG. 8, where aluminum and calcium have a large matching score compared to titanium.

Regarding fusion of multiple spectral lines, an example is presented herein of performing an inference calculation to account for multiple spectral lines. Levels of confidence were sent for metallic samples to initiate the calculations (see FIG. 1), producing an array of inferences that can be made. Each line j has a set of emitters i $\{E_i^j\}$ with attributed probabilities $p(E_i^j)$. The influence of other lines on the set of a first line is unknown, $p(E_i^j|\{E_l^k\})$. Further, the logic maintains that if the de-excitation of the same upper level appears in two spectral lines (i.e., a spectral doublet), then the probability of this element is higher for both lines. By normalization, the other elements would have a lower probability.

FIG. 9 is a chart with exemplary data for level of confidence after single peak analysis without correlation measurements. In addition to this calculation for the single peak, however, a peak matching algorithm can be used to obtain information on the correlation between peaks of each element and an algorithm can be used to merge the information of each peak (called "peak inference" in FIG. 6) in order to refine the calculation of the level of confidence.

The approaches just described can be used alone or in combination in order to provide a correction factor to the score obtained fir each transition during the analysis of each single spectral line.

As an example, if the emission strength is based on the population of the upper level of the transition (energy E and degeneracy g), each transition in the database is attributed the factor:

$$gA/Z(T)\cdot\exp(-E/T)$$

where A is the probability of the transition, T is temperature, and Z(T) the partition function of the ion. In determining probability of population, there is a need for an effective temperature.

It is contemplated that the determination of emission strength can include more plasma parameters such as temperatures, electronic density (better representation of ions), and ion densities (possibly improving on the stoichiometric ablation). These parameters can be used as parameters and/or measured and implemented in the calculation of the emission strength.

Once this emission strength is obtained for each transition considered for a given distribution, it is multiplied by the value of the spectrum/distribution for the wavelength of the transition.

When evaluating the value for signal strength, different values or parameters were tested. Equiprobability was not representative of signal strength. Probability of emission was observed to have issues with ions, even with low temperature plasmas. Population of the upper level was observed to have large dependence and a need for a representative temperature. Thus, measurements of temperature should be performed as well.

The quantitative approach of certain embodiments of the current invention provides a plurality of improvements and advantages over the conventional art, in particular standard LIBS technology. Further, the present invention could consider the signal-to-noise ratio (SNR) by providing a factor representing this SNR that can be included in the calculation.

Algorithm

Figure 5:
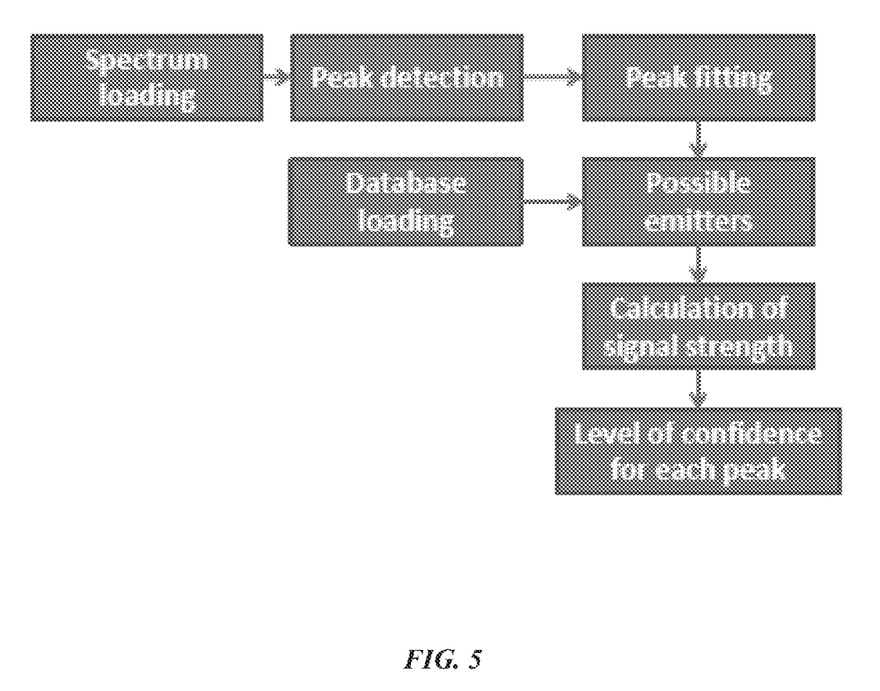
FIG. 5 is a flowchart depicting an exemplary step-by-step algorithm of an embodiment of the current invention.
Figure 6:
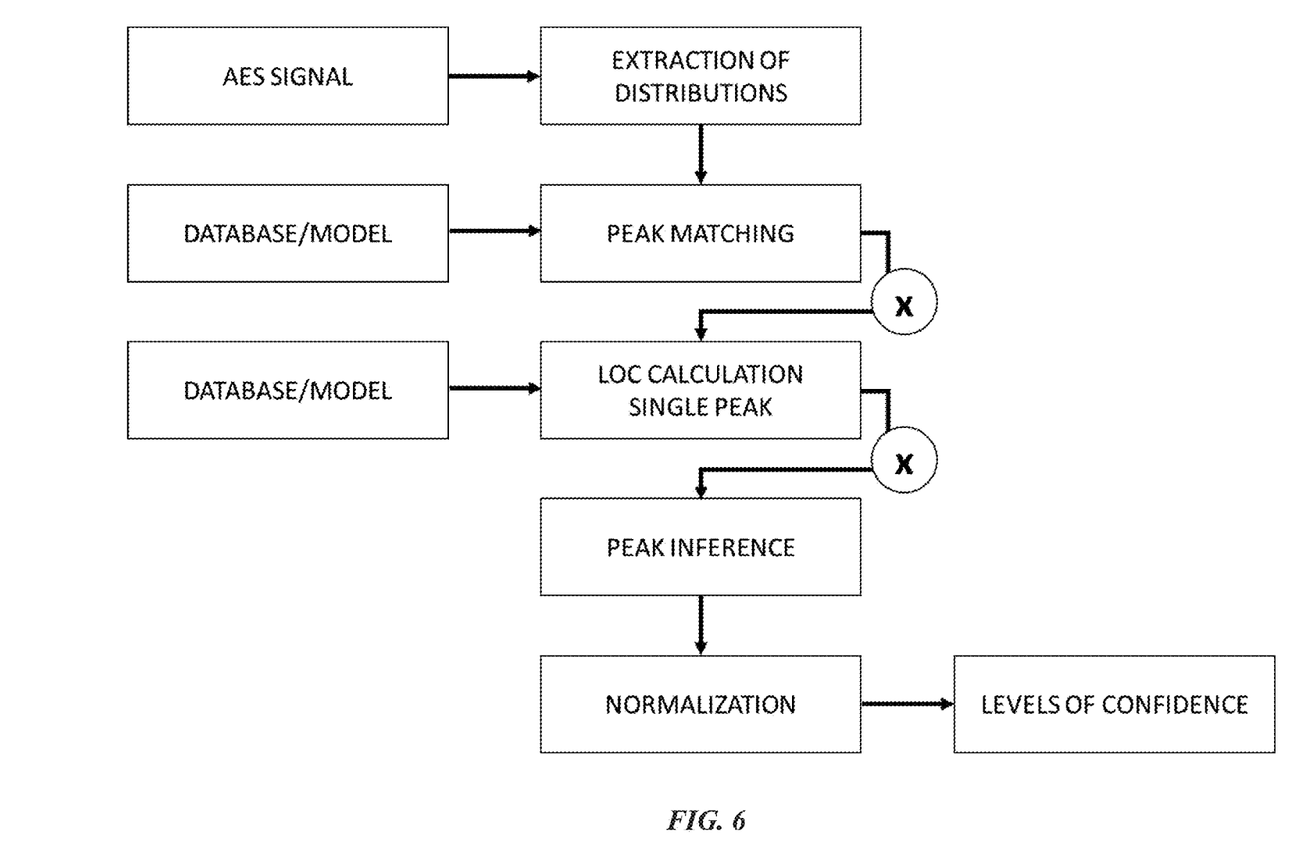
FIG. 6 is a flowchart depicting the algorithm for the calculation of the levels of confidence in each transition for each spectral peak.

FIGS. 5-6 depict step-by-step algorithms of exemplary embodiments of an implemented software application. As seen in FIG. 5, the spectrum is loaded from the instrument and peaks detected. The peaks are fitted to corresponding spectral lines. Possible emitters are then observed from the fitted peaks, using the database previously loaded in the software application. Upon recognition of possible emitters, the spectral lines are normalized to indicate signal strength of each emitter. Then the signal strength of the emitters are calculated, thus leading to a determination of the level of confidence of emitters for each peak.

As seen in FIG. 6, a signal is received, where the signal can indicate atomic interferences and/or molecular interferences. The central position (e.g., central wavelength) for each peak in the signal can be defined, along with the width and shape of the peaks, thus providing density distributions. Once this information is Obtained, the distribution for each peak is extracted. The extracted distributions are then compared to the pre-loaded model/database, where the model/database provides wavelength, emission intensity, entry levels, etc. about the transitions. Emission strength is calculated for each transition that can be found in the database. Each emission strength is then multiplied by the value of the spectrum at the transition wavelength of the distribution (approaches zero (0) as moving further from the peak). Each transition under a spectral peak has a probability that can be normalized to have a sum of one (1) over a certain spectral range to provide a notion of probability. Normalization is defined by the number of transitions considered. This results in the level of confidence for a single peak.

When studying the value for the signal strength, prior knowledge of the composition could be incorporated. Additionally, population of the upper level of the analyte should be evaluated, for example by using measurements of excitation temperature from the spectrum to verify the possibility of using the upper level population. The measurement of electronic density may go further in a plasma model densities and temperatures).

Hardware and Software Infrastructure Examples

The present invention may be embodied on various computing platforms that perform actions responsive to software-based instructions and most particularly on touch-screen portable devices. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C#, C++, Visual Basic or the like and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

It should be noted that when referenced, an "end-user" is an operator of the software as opposed to a developer or author who modifies the underlying source code of the software. For security purposes, authentication means identifying the particular user while authorization defines what procedures and functions that user is permitted to execute.

Glossary of Claim Terms

Analyte: This term is used herein to refer to any substance or composition undergoing spectral analysis. Analytes typically contain more than one elements or emitters that are to be identified and analyzed.

Central position: This term is used herein to refer to a central or averaged wavelength of each peak in a spectrum.

Density distribution: This term is used herein to refer to a function describing the likelihood of a continuous random variable taking on a given value.

Emission strength: This term is used herein to refer to the strength of the absorption, signal, and/or scattering of radiated energy by an emitter or element in the analyte. Emission strength is typically indicated by the spectral line of the emitter.

Emitter information: This term is used herein to refer to any data relating to an element in a composition that radiates energy as a result of being excited, for example by a highly energetic laser pulse.

Emitter: This term is used herein to refer to an element in a composition that radiates energy as a result of being excited, for example by a highly energetic laser pulse.

Inference calculation: This term is used herein to refer to an extrapolation of data to consider other lines relative to a particular line in order to correct that line. The inference calculation simply accounts for multiple spectral lines.

Intensity: This term is used herein to refer to a qualitative measurement of signal strength.

Intensity: This term is used herein to refer to the height of each peak in a spectrum.

Level of confidence: This term is used herein to refer to a measurement of accuracy in the assignment of a spectral line to a peak in the spectrum.

Level of confidence: This term is used herein to refer to the measurement of the accuracy and precision of assignment of a spectral line in the spectrum.

Multimodal probability distribution: This term is used herein to refer to a continuous probability distribution with a plurality a modes. The probability density function of the distribution provides the likelihood of a continuous random variable taking on a given value.

Normalize: This term is used herein to refer to formatting or standardizing certain values so that they can be compared or analyzed against each other as part of a whole. For example, values can be standardized to a percentage of a 100% whole, so that they can be compared to each other.

Oscillator strength: This term is used herein to refer to the probability of absorption or emission of electromagnetic radiation in transitions between energy levels of an atom or molecular.

Possible emitter: This term is used herein to refer to element in the analyzed composition that could feasibly be identified as being associated with a spectral peak, based on spectral information given in the database. There typically is not a threshold level of matching to the spectral database that must be achieved in order to identify possible emitters. Rather, if a possible emitter is identified but does not match the database, then there will be n low level of confidence in the assignment of that peak.

Probability of assignment: This term is used herein to refer to the likelihood of that a particular emitter is actually associated with a peak seen in the spectrum.

Spectral database: This term is used herein to refer to a collection of information regarding the assignment of spectral lines to peaks.

Spectral information: This term is used herein to refer to any data relating to the identification, assignment, or analysis of a spectral peak. Examples include, but are not limited to, the position of the peak in the spectrum, the strength of the absorption/emission/scattering, and additional technical details on the physics of the transition.

Spectral peak information: This term is used herein to refer to any data relating a signal on a spectrum.

Spectral line: This term is used herein to refer to the estimated value of radiated energy of an emitter or element, where the peak representing the radiated energy is assigned a corresponding spectral line based on data compiled in the spectral database (e.g., NIST).

Spectral peak: This term is used herein to refer to a measurement of the excitation of an emitter in a composition.

Spectrum: This term is used herein to refer to a plot showing intensity vs. mass-to-charge ratio in a particular chemical analysis of a composition.

Upper level population: This term is used herein to refer to the population of the upper energy level involved in an emission transition.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. One or more tangible non-transitory computer-readable media having computer-executable instructions for performing a method of running a software program on a computing device, the computing device operating under an operating system, the method including issuing instructions from the software program to analyze an analyte via atomic emission spectroscopy, the instructions comprising:

receiving a spectral database containing spectral information, said spectral information including spectral peak information and emitter information associated with said spectral peak information;

receiving an atomic emission spectrum including one or more spectral peaks associated with an emitter of said analyte, said spectrum being a multimodal probability distribution over a variable being wavelength of emitters;

identifying possible emitters associated with said one or more spectral peaks based on said spectral information in said spectral database, said identification based on a comparison of each individual peak of said one or more spectral peaks to said spectral information contained in said spectral database, wherein each of said possible emitters has a wavelength;

determining emission strength of said wavelength of said each possible emitter for said one or more spectral peaks, said emission strength associated with intensity of said each possible emitter of said one or more spectral peaks;

normalizing said emission strength of said each possible emitter to a probability range such that a sum of resulting probabilities of assignments of said each possible emitter of said one or more spectral peaks equals about 100% over a spectral range, said normalization of said one or more spectral peaks indicating said emission strength of said possible emitters, such that said emission strength of said each possible emitter is utilized as a probability for assignment of said each possible emitter with said wavelength of said each possible emitter being said variable for said multimodal probability distribution in order to determine probability of said assignment of said each possible emitter in said spectrum; and automatically determining a level of confidence of identification of said each possible emitter based on said resulting probabilities of assignments of said possible emitters.

2. One or more tangible non-transitory computer-readable media as in claim 1, further comprising:

said emission strength being selected from the group consisting of an upper level population or an oscillator strength of said possible emitters.

3. One or more tangible non-transitory computer-readable media as in claim 2, further comprising:

said oscillator strength included in said spectral database.

4. One or more tangible non-transitory computer-readable media as in claim 1, further comprising:

said one or more spectral peaks being a plurality of spectral peaks, performing the foregoing steps to determine said level of confidence for assignment of each of said plurality of spectral peaks; and performing an inference calculation to correct for inference and dependency between or among said plurality of spectral peaks.

5. One or more tangible non-transitory computer-readable media as in claim 1, further comprising:

correcting for a background of said spectrum and extracting noise from said spectrum to facilitate said spectrum being said multimodal probabilistic distribution.

6. One or more tangible non-transitory computer-readable media as in claim 1, wherein the step of normalizing said emission strength is performed by multiplying said emission strength by a value of the spectrum at a wavelength of said emitter.

7. One or more tangible non-transitory computer-readable media as in claim 1, further comprising:

generating a profile of said spectrum based on said level of confidence calculated for said each possible emitter.

8. A computer-implemented method of automatically quantitatively determining a level of confidence for identification of an emitter represented by a spectral peak obtained via atomic emission spectroscopy, comprising:

receiving a spectral database containing spectral information, said spectral information including spectral peak information and emitter information associated with said spectral peak information;

receiving an atomic emission spectrum including one or more spectral peaks associated with an emitter of an analyte, said spectrum being a multimodal probability distribution over a variable being wavelength of emitters;

identifying possible emitters associated with said one or more spectral peaks based on said spectral information in said spectral database, said identification based on a comparison of each individual peak of said one or more spectral peaks to said spectral information contained in said spectral database, wherein each of said possible emitters has a wavelength;

determining emission strength of said wavelength of said each possible emitter for said one or more spectral peaks, said emission strength associated with intensity of said each possible emitter of said one or more spectral peaks;

normalizing said emission strength of said each possible emitter to a probability range such that a sum of resulting probabilities of assignments of said each possible emitter of said one or more spectral peaks equals about 100% over a spectral range, said normalization of said one or more spectral peaks indicating said emission strength of said possible emitters, such that said emission strength of said each possible emitter is utilized as a probability for assignment of said each possible emitter with said wavelength of said each possible emitter being said variable for said multimodal probability distribution in order to determine probability of said assignment of said each possible emitter in said spectrum; and automatically determining a level of confidence of identification of said each possible emitter based on said resulting probabilities of assignments of said possible emitters.

9. A computer-implemented method as in claim 8, further comprising:

said emission strength being selected from the group consisting of an upper level population or an oscillator strength of said possible emitters.

10. A computer-implemented method as in claim 9, further comprising:

said oscillator strength included in said spectral database.

11. A computer-implemented method as in claim 8, further comprising:

said one or more spectral peaks being a plurality of spectral peaks, performing the foregoing steps to determine said level of confidence for assignment of each of said plurality of spectral peaks; and performing an inference calculation to correct for inference and dependency between or among said plurality of spectral peaks.

12. A computer-implemented method as in claim 8, further comprising:

correcting for a background of said spectrum and extracting noise from said spectrum to facilitate said spectrum being said multimodal probabilistic distribution.

13. A computer-implemented method as in claim 8, wherein the step of normalizing said emission strength is performed by multiplying said emission strength by a value of the spectrum at a wavelength of said emitter.

14. A computer-implemented method as in claim 8, further comprising:

generating a profile of said spectrum based on said level of confidence calculated for said each possible emitter.

15. One or more tangible non-transitory computer-readable media having computer-executable instructions for performing a method of running a software program on a computing device, the computing device operating under an operating system, the method including issuing instructions from the software program to analyze an analyte via atomic emission spectroscopy, the instructions comprising:

receiving a spectral database containing spectral information, said spectral information including spectral peak information and emitter information associated with said spectral peak information;

receiving an atomic emission spectrum including one or more spectral peaks associated with an emitter of said analyte, said spectrum being a multimodal probability distribution over a variable being wavelength of emitters;

defining a central position for each peak of said one or more peaks in order to provide a density distribution for said each peak in said multimodal probability distribution;

extracting a probability distribution from said each density distribution;

comparing said extracted probability distribution to said spectral database to identify possible emitters that are present in each individual peak of said one or more spectral peaks;

determining emission strength for each emitter of said possible emitters, said emission strength associated with intensity of said each possible emitter of said one or more spectral peaks;

normalizing said emission strength of said each possible emitter to a probability range such that a sum of resulting probabilities of assignments of said each possible emitter of said one or more spectral peaks equals about 100% over a spectral range, said normalization of said one or more spectral peaks indicating said emission strength of said possible emitters, such that said emission strength of said each possible emitter is utilized as a probability for assignment of said each possible emitter with said wavelength of said each possible emitter being said variable for said multimodal probability distribution in order to determine probability of said assignment of said each possible emitter in said spectrum;

calculating a level of confidence for said each emitter based on said normalized emission strength of said each emitter;

as a result of said one or more spectral peaks being a plurality of spectral peaks present in said spectrum, performing the foregoing steps to determine said level of confidence for assignment of each of said plurality of spectral peaks;

performing an inference calculation to correct for inference and dependency between or among said plurality of spectral peaks;

normalizing said plurality of spectral peaks to a probability range such that a sum of resulting probabilities of assignments of said each spectral peak equals about 100% over a spectral range, such that said resulting probabilities indicate a probability for assignment of said each spectral peak with said wavelength of said each emitter being said variable for said multimodal probability distribution; and automatically calculating a level of confidence of identification of said each spectral peak based on said resulting probabilities of assignments of said possible emitters.

16. One or more tangible non-transitory computer-readable media as in claim 15, wherein the step of normalizing said plurality of spectral peaks includes multiplying said emission strength by a value of the spectrum at a given wavelength of said each emitter in said probability distribution.

17. One or more tangible non-transitory computer-readable media as in claim 15, further comprising:

said emission strength being selected from the group consisting of an upper level population or an oscillator strength of said possible emitters.

18. One or more tangible non-transitory computer-readable media as in claim 17, further comprising:

said oscillator strength included in said spectral database.

19. One or more tangible non-transitory computer-readable media as in claim 15, further comprising:

correcting for a background of said spectrum and extracting noise from said spectrum to facilitate said spectrum being said multimodal probabilistic distribution.

20. One or more tangible non-transitory computer-readable media as in claim 15, further comprising:

generating a profile of said spectrum based on said level of confidence calculated for said each spectral peak.

* * * * *